(12) United States Patent
Israel

(10) Patent No.: US 6,994,721 B2
(45) Date of Patent: Feb. 7, 2006

(54) STENT ASSEMBLY

(76) Inventor: Henry M. Israel, 39 Ben Zakai Street, Bnei Brak 51482 (IL)

( * ) Notice: Subject to any disclaimer, the term of this patent is extended or adjusted under 35 U.S.C. 154(b) by 445 days.

(21) Appl. No.: 10/274,037

(22) Filed: Oct. 21, 2002

(65) Prior Publication Data

US 2004/0093067 A1 May 13, 2004

(51) Int. Cl.
*A61M 2/06* (2006.01)

(52) U.S. Cl. ............... 623/1.11; 623/1.12; 623/1.13
(58) Field of Classification Search ....... 623/1.11–1.15, 623/1, 1.23, 1.35; 606/194–195, 108
See application file for complete search history.

(56) References Cited

U.S. PATENT DOCUMENTS

| 5,201,757 A | * | 4/1993 | Heyn et al. ............... 606/198 |
| 6,063,112 A | * | 5/2000 | Sgro ............................ 623/1.12 |
| 6,210,429 B1 | * | 4/2001 | Vardi et al. ................. 623/1.11 |
| 6,224,609 B1 | * | 5/2001 | Ressemann et al. ......... 606/108 |
| 6,432,130 B1 | * | 8/2002 | Hanson ...................... 623/1.11 |
| 6,500,202 B1 | * | 12/2002 | Shaolian et al. ........... 623/1.11 |

* cited by examiner

*Primary Examiner*—Tan-Uyen T. Ho
(74) *Attorney, Agent, or Firm*—Dekel Patent Ltd.; David Klein

(57) ABSTRACT

A stent assembly comprises a stent sheath that includes distally and proximally removable portions separable from one another by manipulation of first and second guidewires, a contracted stent having a side aperture disposed in the stent sheath and a third guidewire extending between the removable portions and through the side aperture of the stent.

12 Claims, 3 Drawing Sheets

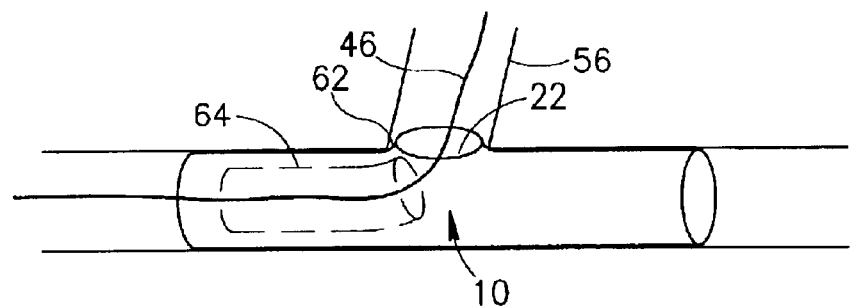
FIG. 7
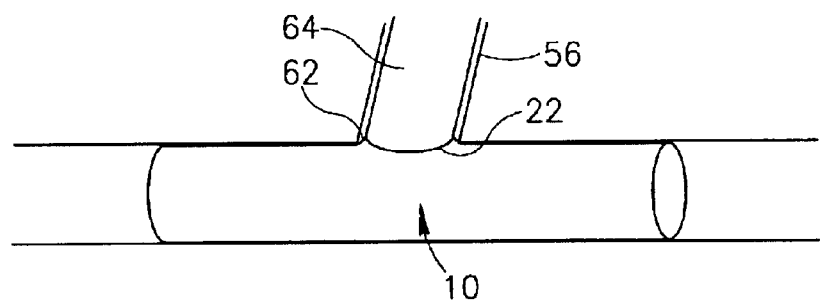
FIG. 8
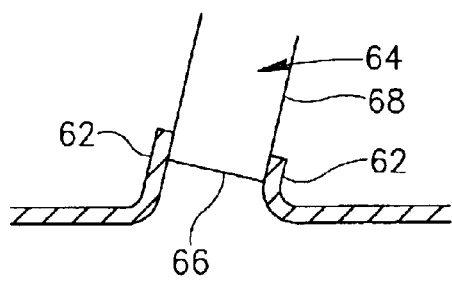 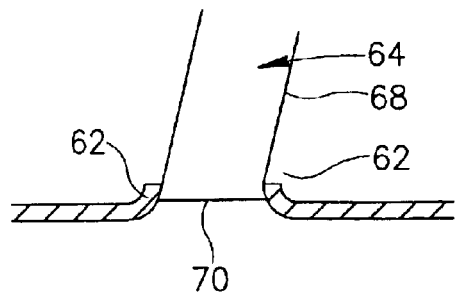
FIG. 9A FIG. 9B

STENT ASSEMBLY

FIELD OF THE INVENTION

The present invention relates generally to stents, and particularly to bifurcated stents.

BACKGROUND OF THE INVENTION

A stent is a well known device used to support an intraluminal wall, used in procedures, such as but not limited to, percutaneous transluminal coronary angioplasty (PTCA). Various types of stent architectures are known in the art, including braided stents (filaments or wires, wound or braided into a particular configuration), or mesh stents (metal mesh bent or formed into a particular shape), among others.

Typically, a stent may be restrained in a radially compressed configuration by a sheath or catheter, and delivered by a deployment system or "introducer" to the site where it is required. The introducer may enter the body through the patient's skin, or through a blood vessel exposed by minor surgical means. When the introducer has been threaded into the body lumen to the stent deployment location, the introducer is manipulated to cause the stent to be released. The stent expands to a predetermined diameter at the deployment location, and the introducer is withdrawn. Stent expansion may be effected by spring elasticity, balloon expansion, or by the self-expansion of a thermally or stress-induced return of a shape memory alloy (such as a nickel-titanium alloy, e.g., NITINOL) to a pre-conditioned expanded configuration.

There are bifurcated lumens, such as but not limited to, the carotid artery, which may need support with a bifurcated stent. A bifurcated lumen (also called bifurcation) is an area of the vasculature where a first vessel is bifurcated into two or more branch vessels. Stenotic lesions may form in or around such bifurcations, that is, in or around one or more of the vessels.

However, delivering and deploying a stent to support a bifurcated lumen is a difficult challenge. Some of the problems include the difficulty of properly orienting the stent with respect to the bifurcation and the difficulty of providing a stent that supports the main trunk and branches of the bifurcation without blocking the passageways or causing turbulence or other flow disruptions.

SUMMARY OF THE INVENTION

The present invention seeks to provide a bifurcated stent assembly that may be disposed in a bifurcated lumen and which may overcome the abovementioned problems of the prior art.

There is thus provided in accordance with an embodiment of the present invention a stent assembly comprising a stent sheath that includes two individually removable portions. A stent may be disposed in the sheath in a contracted orientation.

In accordance with an embodiment of the present invention the removable portions comprise a distally removable portion and a proximally removable portion.

Further in accordance with an embodiment of the present invention the removable portions may be joined by a rupturable element.

Still further in accordance with an embodiment of the present invention the distally removable portion comprises a distal cap configured to facilitate movement of the stent assembly in a vasculature.

In accordance with an embodiment of the present invention at least one guidewire is attached to a portion of the stent assembly for manipulation thereof.

Further in accordance with an embodiment of the present invention one of the removable portions of the sheath is removable by distally sliding off the stent.

In accordance with an embodiment of the present invention the stent comprises a distal portion and a proximal portion connected by a flexible portion. The flexible portion may have axial flexibility and/or torsional flexibility.

Further in accordance with an embodiment of the present invention the stent is formed with a side aperture and a flange-forming structure at least partially surrounding the aperture.

Still further in accordance with an embodiment of the present invention the flange-forming structure is expandable to form a flange.

Additionally in accordance with an embodiment of the present invention the flange is connectable to a branch stent. An end face of the branch stent may be oblique to a side wall of the branch stent, or the flange may have an oblique shape.

There is also provided in accordance with an embodiment of the present invention a stent assembly comprising a stent formed with a side aperture and a flange-forming structure at least partially surrounding the aperture, wherein the flange-forming structure is expandable to form a flange.

There is also provided in accordance with an embodiment of the present invention a method comprising providing a stent in a stent sheath, the sheath being maneuverable by a proximally extending guidewire, and removing the sheath distally off the stent.

In accordance with an embodiment of the present invention the sheath comprises a distally removable portion and a proximally removable portion, and the method further comprises removing the distally removable portion distally off the stent and removing the proximally removable portion proximally off the stent. The distally removable portion and the proximally removable portion may be removed simultaneously or one after another off the stent. Alternatively, either one of the distally removable portion and the proximally removable portion may be removed off the stent and the other removable portion may be left.

BRIEF DESCRIPTION OF DRAWINGS

The present invention will be further understood and appreciated from the following detailed description taken in conjunction with the drawing in which:

FIG. 7 is a simplified illustration of the stent assembly of FIG. 2, wherein a branch stent has been introduced through the side aperture to the bifurcation, in accordance with an embodiment of the invention;

FIG. 8 is a simplified illustration of the stent assembly of FIG. 2, wherein the branch stent is affixed to the stent of the stent assembly and is expanded in place in the bifurcation, in accordance with an embodiment of the invention; and FIGS. 9A and 9B are more detailed illustrations of two possible attachments of the branch stent to the stent of the stent assembly.

DETAILED DESCRIPTION OF THE INVENTION

Figure 1:
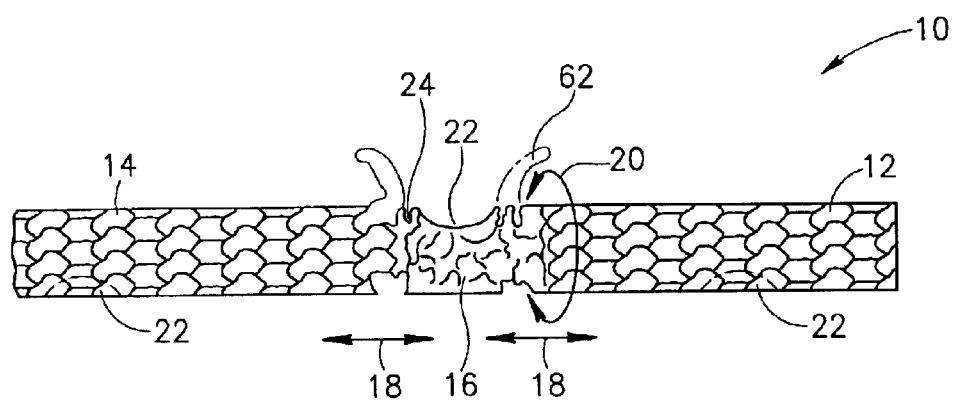
FIG. 1 is a simplified pictorial illustration of a stent, constructed and operative in accordance with an embodiment of the invention.

Reference is now made to FIG. 1, which illustrates a stent 10, constructed and operative in accordance with an embodiment of the invention. Stent 10 is illustrated as a uniform wire mesh stent, but the invention is not limited to this construction. Stent 10 may comprise a distal portion 12 and a proximal portion 14 connected by a flexible portion 16 (of same or different diameters). Flexible portion 16 may provide axial flexibility in a longitudinal direction indicated by arrows 18 and/or torsional flexibility in a radial direction indicated by arrows 20. Stent 10 may be balloon-expandable, constructed from a suitable material, such as but not limited to, stainless steel 316L, or self-expanding, constructed from a suitable material, such as but not limited to, a shape memory alloy (such as a nickel-titanium alloy, e.g., NITINOL). Stent 10 may be formed with a side aperture 22 in any of the abovementioned portions thereof, namely, in flexible portion 16 (aperture 22 being shown there in solid lines in FIG. 1), or in distal portion 12 or proximal portion 14 (aperture 22 being shown there in phantom lines in FIG. 1). Stent 10 may alternatively be any kind of bifurcated stent.

Stent 10 may further comprise a flange-forming structure 24 at least partially surrounding aperture 22. The flange-forming structure 24 may be constructed of a wire mesh pattern, for example, which upon expansion may form a flange 62 (shown in phantom lines in FIG. 1). The expansion of flange-forming structure 24 may be accomplished by any suitable method, such as but not limited to, expansion with a balloon, flexure or self-expansion by the flexibility or shape-memory properties of the material or by being pushed out by some object (not shown) introduced to the area of aperture 22.

Figure 2:
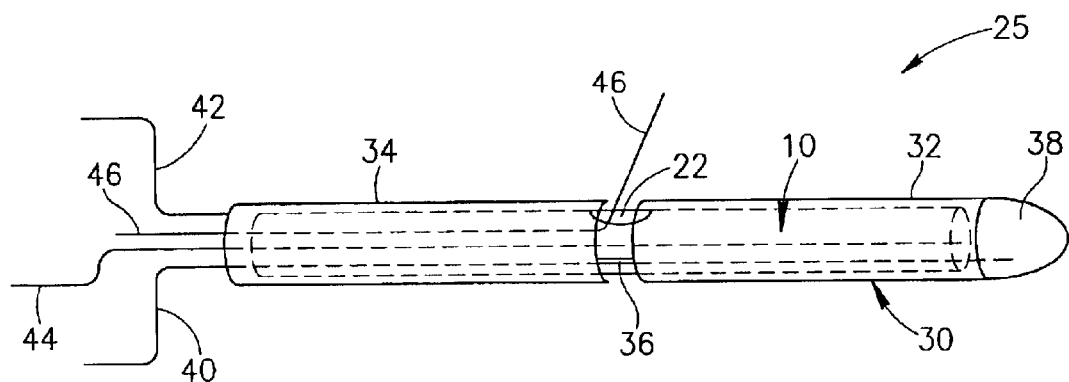
FIG. 2 is a simplified illustration of a stent assembly comprising the stent of FIG. 1, and also comprising a sheath with a distally removable portion and a proximally removable portion, constructed and operative in accordance with an embodiment of the invention.

Reference is now made to FIG. 2, which illustrates a stent assembly 25 comprising stent 10 of FIG. 1, constructed and operative in accordance with an embodiment of the invention. Stent assembly 25 may comprise a stent sheath 30 in which stent 10 is initially disposed in a contracted orientation prior to deployment. Sheath 30 may include two individually removable portions 32 and 34, which may be separable from one another. In the illustrated embodiment, sheath 30 comprises a distally removable portion 32 and a proximally removable portion 34. Distally removable portion 32 and proximally removable portion 34 may be completely separate from one another. Optionally, they may be initially joined by a rupturable element 36, such as but not limited to, a thin strip, wherein the rupturable element 36 may be severed, cut, ruptured, broken or otherwise removed so that the two portions 32 and 34 may be individually removed, as described hereinbelow. Distally removable portion 32 may comprise a distal cap 38, configured (e.g., preferably smooth and rounded) to facilitate movement of the stent assembly 25 in the vasculature.

Guidewires are preferably attached to portions of stent assembly 25 for manipulation thereof. For example, a guidewire 40 may be attached to distally removable portion 32; a guidewire 42 may be attached to proximally removable portion 34; a guidewire 44 may be attached to stent 10, such as at a distal end thereof; and a guidewire 46 may be provided for passing through side aperture 22. The guidewires may be grasped and manipulated at the proximal end of a stent deployment catheter (not shown) as is well known in the art.

Figure 3:
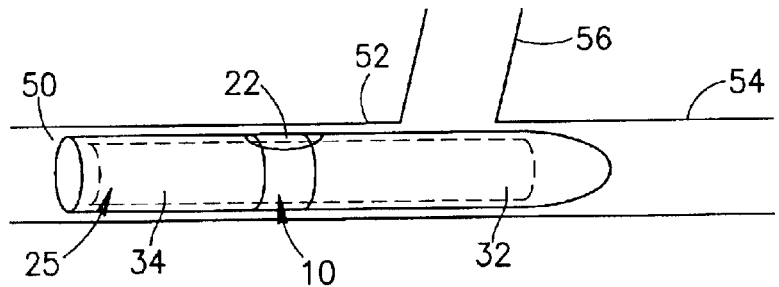
FIG. 3 is a simplified illustration of the stent assembly of FIG. 2 introduced into a body lumen that has a bifurcation, in accordance with an embodiment of the invention.

Reference is now made to FIG. 3, which illustrates stent assembly 25 introduced into a body lumen 50 that has a bifurcation comprising trunk 52 and branches 54 and 56, in accordance with an embodiment of the invention. The stent deployment catheter (not shown) may be used to deliver stent assembly 25 into body lumen 50.

Figure 4:
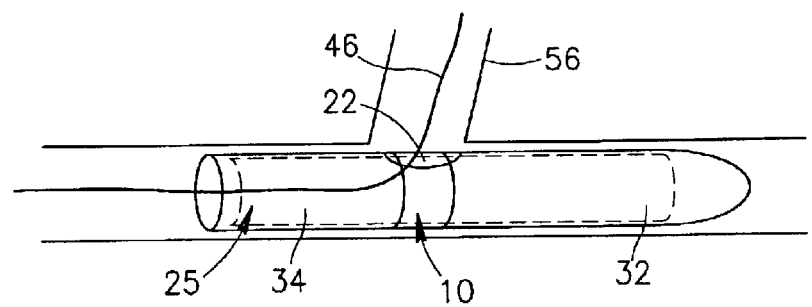
FIG. 4 is a simplified illustration of the stent assembly of FIG. 2 positioned in the body lumen such that a guide wire protrudes from a side aperture formed in the stent into a branch of the bifurcation, in accordance with an embodiment of the invention.

Reference is now made to FIG. 4, which illustrates stent assembly 25 positioned in body lumen 50 such that side aperture 22 is aligned with branch 56 of the bifurcation. Guide wire 46 may be manipulated to protrude from side aperture 22 into branch 56.

Figure 5:
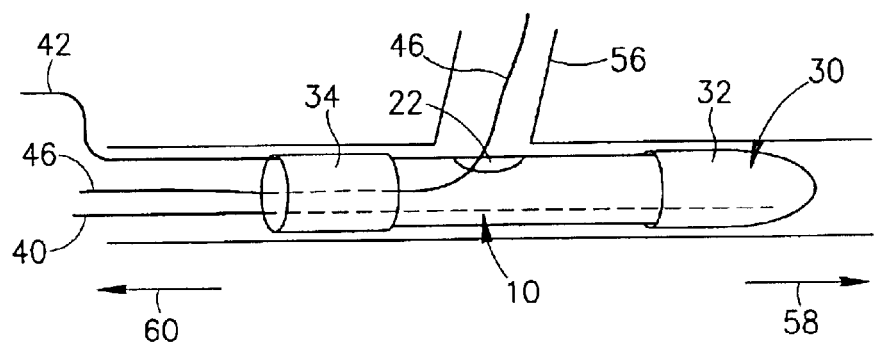
FIG. 5 is a simplified illustration of removing the distally removable portion and the proximally removable portion of the sheath of the stent assembly of FIG. 2, in accordance with an embodiment of the invention.
Figure 6:
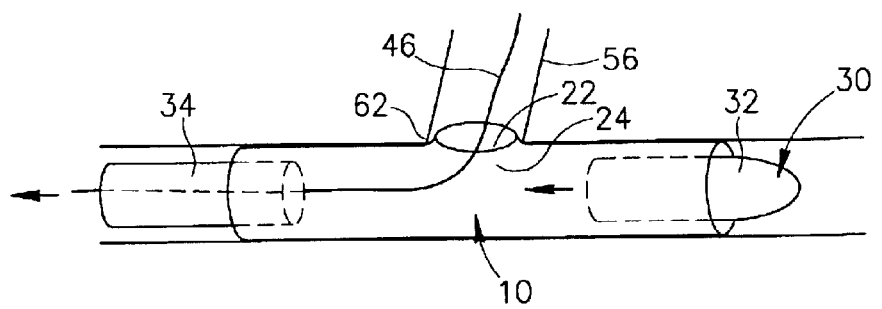
FIG. 6 is a simplified illustration of the stent assembly of FIG. 2, wherein the stent has expanded and the side aperture forms a flange at the bifurcation, in accordance with an embodiment of the invention.

Reference is now made to FIG. 5, which illustrates one method of deploying stent 10 in the bifurcation. The distally removable portion 32 of sheath 30 may be removed by distally slipping (sliding) it off stent 10 by distally pushing with guidewire 40 (as indicated by an arrow 58). The proximally removable portion 34 of sheath 30 may be removed by proximally slipping (sliding) it off stent 10 by proximally pulling with guidewire 42 (as indicated by an arrow 60). Distally removable portion 32 and proximally removable portion 34 of sheath 30 may be removed simultaneously or one after the other or individually. (By individually it is meant that either one of the distally removable portion 32 and the proximally removable portion 34 is removed off stent 10 and the other removable portion is left on stent 10.) After their removal, as seen in FIG. 6, sheath 10 expands and is affixed to the bifurcation, wherein aperture 22 is aligned with branch 56. Upon expansion of stent 10, the flange-forming structure 24 may also expand to form a flange 62 which may hug and overlap the juncture of branch 56 with the bifurcation. The distally removable portion 32 of sheath 30 may be removed from the vasculature by pulling it proximally through stent 10, since the expanded stent 10 now has a larger diameter than the sheath 30. The proximally removable portion 34 of sheath 30 may also be removed from the vasculature.

In accordance with another embodiment of the invention, sheath 30 may comprise distally removable portion 32 without proximally removable portion 34. Sheath 30 may be removed from stent 10 by distally sliding distally removable portion 32 off stent 10. Stent 10 then expands to a larger diameter than the sheath 30, and distally removable portion 32 of sheath 30 may be removed from the vasculature by pulling it proximally through stent 10, as mentioned before.

Reference is now made to FIG. 7, which illustrates introducing a branch stent 64 through side aperture 22 to the bifurcation. The branch stent 64 may also be a self-expanding wire mesh stent constructed from a shape memory alloy, but the invention is not limited to this construction. The branch stent 64 may be introduced with a conventional sheath and catheter (not shown) as well known in the art.

Reference is now made to FIG. 8, which illustrates branch stent 64 expanded in place in branch 56. Branch stent 64 may be affixed to flange 62 of stent 10. For example, branch stent 64 may snap-fit or press-fit together with flange 62, or by any other joining means.

Reference is now made to FIGS. 9A and 9B, which illustrate two possible attachments of branch stent 64 to flange 62. In FIG. 9A, branch stent 64 has an end face 66 which is more or less perpendicular to a side wall 68 of branch stent 64. In such a case, flange 62 may be formed with a tilted configuration, that is, with an oblique shape, so as to better envelop and hold branch stent 64 around its periphery. In FIG. 9B, branch stent 64 has an end face 70 which is oblique to a side wall 68 of branch stent 64. In such a case, the obliqueness of branch stent 64 permits forming flange 62 with a uniform, non-oblique shape.

It will be appreciated that the invention is not limited to what has been described hereinabove merely by way of example. Rather, the invention is limited solely by the claims that follow.

What is claimed is:

1. A stent assembly comprising a stent sheath that includes a distally removable portion and a proximally removable portion, wherein a first guidewire is connected to the distally removable portion and a second guidewire is connected to the proximally removable portion, the guidewires being arranged such that manipulation of said first guidewire distally removes said distally removable portion from said stent sheath and manipulation of said second guidewire proximally removes said proximally removable portion from said stent sheath and further comprising a stent disposed in said sheath in a contracted orientation, wherein said stent is formed with a side aperture, and a third guidewire extends between said removable portions and through the side aperture of said stent.

2. The stent assembly according to claim 1, wherein said removable portions are joined by a rupturable element.

3. The stent assembly according to claim 1, wherein said distally removable portion comprises a distal cap configured to facilitate movement of the stent assembly in a vasculature.

4. The stent assembly according to claim 1, wherein one of said removable portions of said sheath is removable by distally sliding off said stent.

5. The stent assembly according to claim 1, wherein said stent comprises a distal portion and a proximal portion connected by a flexible portion.

6. The stent assembly according to claim 5, wherein said flexible portion has at least one of axial flexibility and torsional flexibility.

7. The stent assembly according to claim 1, wherein said stent further includes a flange-forming structure at least partially surrounding said side aperture.

8. The stent assembly according to claim 7, wherein said flange-forming structure is expandable to form a flange.

9. The stent assembly according to claim 8, wherein said flange is connectable to a branch stent.

10. The stent assembly according to claim 8, further comprising a branch stent connected to said flange.

11. The stent assembly according to claim 10, wherein an end face of said branch stent is oblique to a side wall of said branch stent.

12. The stent assembly according to claim 10, wherein said flange has an oblique shape.

\* \* \* \* \*